United States Patent
Teh

Patent Number: 5,514,110
Date of Patent: May 7, 1996

[54] AUTOMATIC FLOW CONTROL DEVICE

[76] Inventor: Eutiquio L. Teh, 2440 Tiebout Ave. #2, Bronx, N.Y. 10458

[21] Appl. No.: 262,371

[22] Filed: Jun. 20, 1994

Related U.S. Application Data

[63] Continuation-in-part of Ser. No. 34,116, Mar. 22, 1993, abandoned.

[51] Int. Cl.$^6$ .................................................. A61M 5/00
[52] U.S. Cl. ........................ 604/247; 137/517; 604/256; 604/246; 604/249
[58] Field of Search ............................... 604/30, 31, 33, 604/67, 65, 246, 247, 249, 323, 335, 407, 256; 137/498, 503, 504, 517

[56] References Cited

U.S. PATENT DOCUMENTS

| | | | |
|---|---|---|---|
| 934,286 | 9/1909 | Cole | 137/517 |
| 2,245,271 | 6/1941 | Guill | 137/517 |
| 3,109,426 | 11/1963 | Noonan et al. | 604/33 |
| 4,324,239 | 4/1982 | Gordon et al. | 604/256 |
| 4,361,147 | 11/1982 | Aslanian et al. | 604/33 |
| 4,429,856 | 2/1984 | Jackson | 251/149.1 |
| 4,497,468 | 2/1985 | Hubbard et al. | 604/249 X |
| 4,957,483 | 9/1990 | Gonser et al. | 604/246 X |
| 5,019,055 | 5/1991 | O'Boyle | 604/249 |

*Primary Examiner*—Corrine M. Maglione
*Assistant Examiner*—N. Kent Gring
*Attorney, Agent, or Firm*—Fitzpatrick, Cella, Harper & Scinto

[57] ABSTRACT

An intravenous fluid flow control device includes a rigid casing having a fluid entrance and a fluid exit. A portion of the casing has a flow restrictor. A pin is disposed inside the casing and axially movable within the flow restrictor. The pin has an interior passageway and at least one upstream opening for a fluid to pass from the casing fluid entrance to the interior passageway of the pin. The upstream opening is elongated in a direction parallel to a pin longitudinal axis, the pin elongated opening being axially movable within the flow restrictor to variably restrict a flow of the fluid passing through the interior passageway of the pin. The pin has a downstream opening for fluid to pass from the interior passageway of the pin to exit the device. Biasing structure (preferably a spring) biases the pin against a fluid pressure of the fluid entering from the casing fluid entrance to cause the pin elongated opening to move with respect to the fluid restrictor. As the incoming fluid pressure increases to a predetermined value, the fluid flow through the elongated opening also increases. As the fluid pressure further increases above the predetermined value, the elongated opening moves within the fluid restrictor to cause the fluid flow through the elongated opening to decrease.

21 Claims, 11 Drawing Sheets

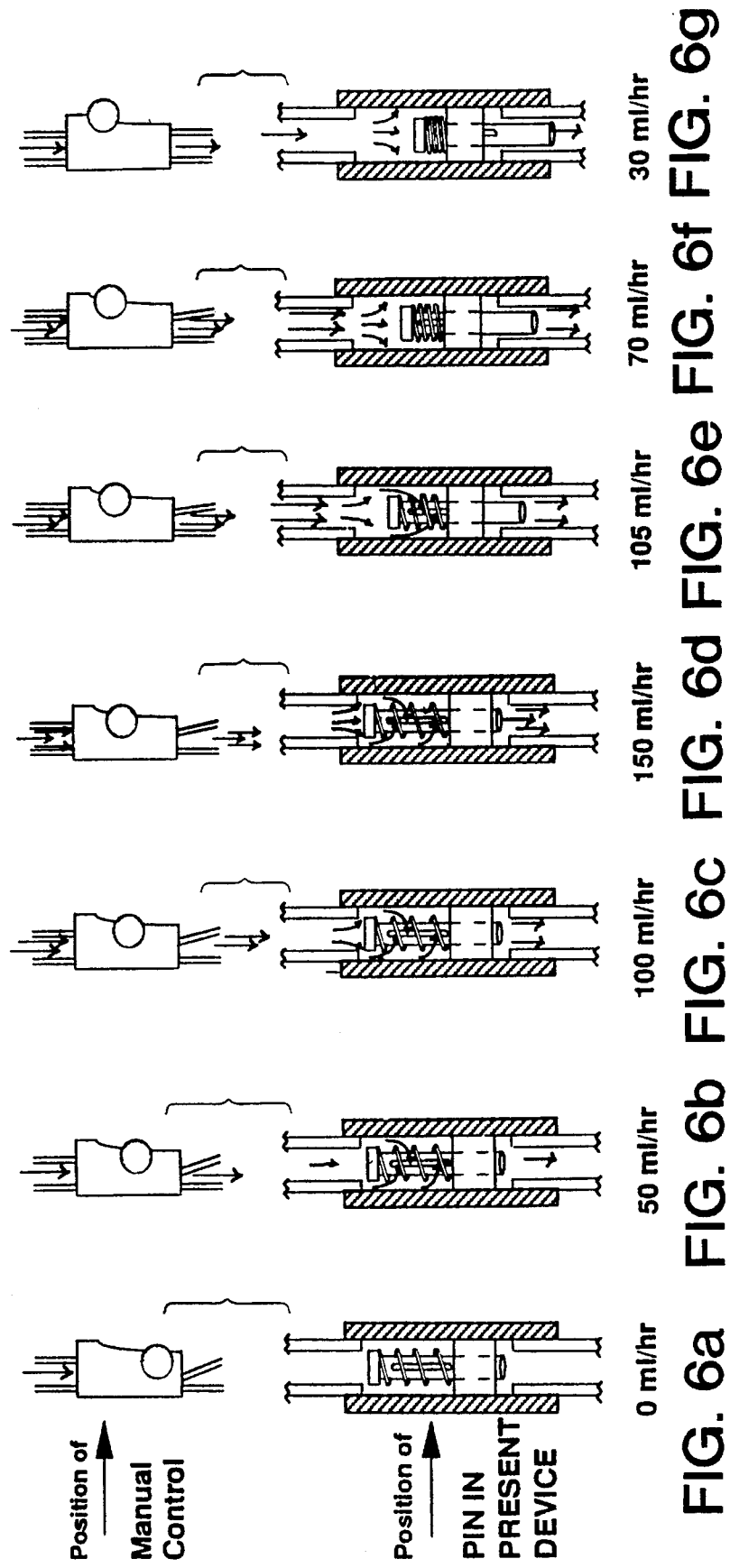

AUTOMATIC FLOW CONTROL DEVICE

This application is a continuation in part of Ser. No. 08/034,116 filed Mar. 22, 1993 now abandoned.

BACKGROUND OF THE INVENTION

1. Field of the Invention

The present invention relates to an inexpensive automatic intravenous flow control device.

2. Description of the prior Art

Devices are known for controlling the flow of intravenous (IV) fluids to a patient. For example, infusion pumps may be used to control the flow of IV fluids to a patient within 10–20% of the prescribed infusion rate. However, infusion pumps are bulky, expensive, and require periodic maintenance.

Simple clamps may be applied to the IV line and may provide acceptable flow control in certain non-critical circumstances. The desired IV drip rate is determined by adjusting the clamp at the beginning of the IV infusion, but must be checked regularly. Because drop size varies with the viscosity of the IV fluid, the drip rate required to give a predictable rate of infusion will vary from solution to solution. Also, changes in the height of the fluid level in the IV container relative to the patient (for example, when the patient sits up or gets out of bed or as the fluid level in the IV container falls) result in changes in the drip rate. This device may be inexpensive but it lacks safety and accuracy.

Variable resistance devices (e.g., Dial-A-Flow by Abbott Laboratories) may also be used as an integral part of the IV line. This device is also sensitive to viscosity changes and requires a constant hydrostatic pressure to maintain constant flow and therefore is subject to the same inaccuracies as the simple clamp discussed above. These devices can be recalibrated for solutions of known viscosity, but such a minor advantage probably fails to justify the increased expense of such devices for routine use.

Gravity-fed pressure-compensating devices (e.g., Isoflux by Geistlich) may also be used to control IV flow. This device has a flexible diaphragm that partially compensates for changes in hydrostatic and venous pressures. While the rate of infusion is more constant and therefore more accurate than the simple clamp, these devices are quite expensive.

Electronic gravity-fed controllers (e.g., Accudot by Imed) are flow control devices that use a variable resistor that is incorporated into the IV set and is adjusted automatically by an electronic controller. Because the controller monitors the drip rate, the infusion rate also varies from solution to solution. However, the rate of flow is not affected by changes in patient position or venous pressure. Again, while the infusion rate is relatively accurate, these controllers are quite expensive.

U.S. Pat. No. 4,361,147 discloses a flow control device for administering IV fluids wherein the fluid flow may be controlled by a spring-biased fluid control cam. Again, such a device is quite expensive to produce.

U.S. Pat. No. 4,324,239 discloses a safety valve for catheterization procedures wherein a piston having an internal flow path is biased by a resilient member such that as fluid pressure increases in the valve, fluid flow through valve also increases. Such a device would be unusable to provide a relatively constant fluid flow through an IV flow controller.

Thus, what is needed is an inexpensive, easy-to-manufacture, easy-to-use IV fluid flow controller that can provide accurate control of fluid flow into the patient. Such a device should be able to be incorporated as an integral part of the IV infusion set so as not to be easily removable.

SUMMARY OF THE INVENTION

An object of the present invention is to provide an inexpensive, easy-to-operate IV fluid flow control device which can accurately control the flow of a fluid into a patient.

According to one aspect of the present invention, an IV fluid flow control device comprises a rigid casing having a fluid entrance and a fluid exit. A fluid restrictor is disposed inside the casing. A pin is disposed inside the casing and is axially movable therein. The pin has at least one upstream opening for the fluid to pass from said casing fluid entrance to an interior passageway of the pin. The upstream opening is disposed adjacent the fluid restrictor to variably restrict the volume of fluid passing to the interior of the pin. The pin also has a downstream opening for the fluid to pass from the interior passageway of the pin to the casing fluid exit. A pin flange is disposed on an upstream end of the pin for contacting the fluid entering from the casing fluid entrance. Biasing means are provided for biasing the pin flange against the fluid pressure entering from the casing fluid entrance to cause the pin upstream opening to move with respect to the fluid restrictor to reduce the flow of fluid through the pin interior passageway when the fluid pressure on the pin flange exceeds a predetermined value.

BRIEF DESCRIPTION OF THE DRAWINGS

The advantageous features according to the present invention will be more readily understood from the following detailed description of the preferred embodiments when taken in conjunction with the attached drawings which show:

FIGS. 6A–6G depict different operating conditions for the FIG. 3 embodiment;

DETAILED DESCRIPTION OF THE PREFERRED EMBODIMENTS

Figures 1, 2:
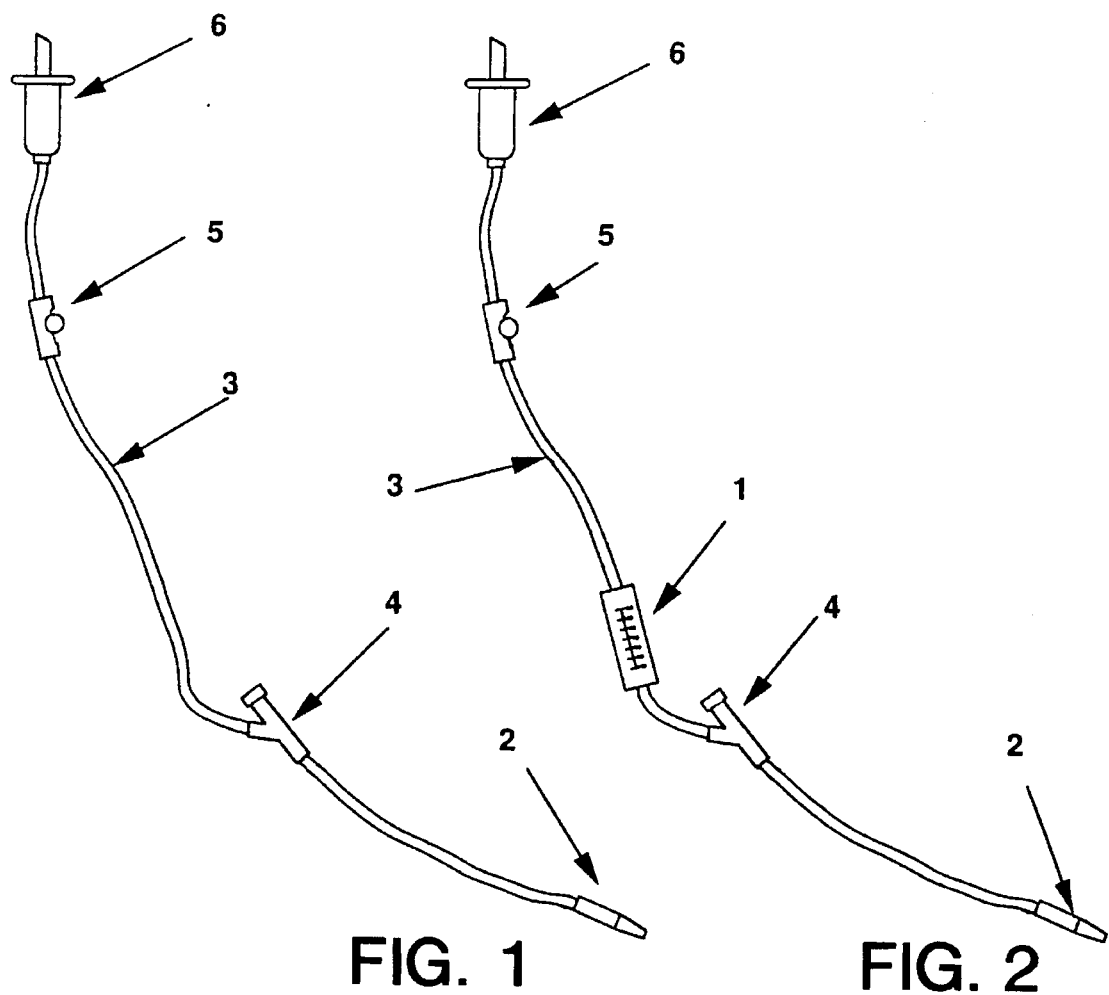
FIG. 1 is a schematic drawing of a prior art IV infusion set such as a "Venoset 78"
FIG. 2 is a schematic drawing of an IV infusion set incorporating the automatic flow control device according to the present invention.

FIG. 1 depicts a prior art IV flow control device such as a "Venoset 78" in which IV fluid enters a drip chamber 6, passes through a manual flow control device 5, passes down plastic IV tubing 3, to the Y-injection site 4 and to the male adaptor 2 which is coupled to a venipucture device (now shown).

FIG. 2 shows the automatic flow control device 1 according to the present invention installed in the FIG. 1 IV set between the Y-injection site 4 and the control device 5.

Figure 3:
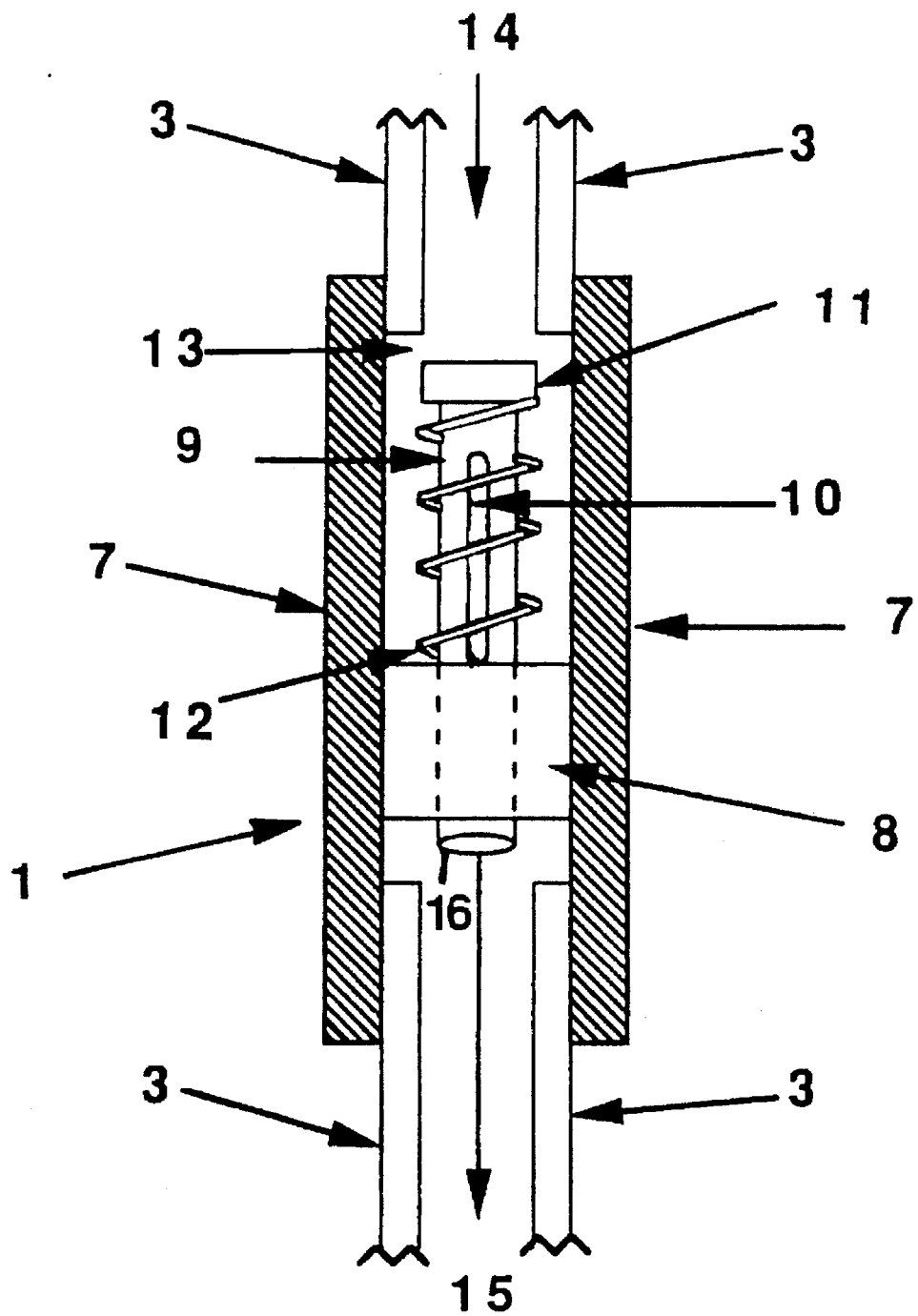
FIG. 3 is a schematic partial cross-section of a first embodiment according to the present invention.

FIG. 3 shows a first embodiment according to the present invention wherein the flow control device 1 is coupled to IV plastic tubing 3. The device 1 has a rigid, transparent plastic casing 7 having a flow-restricting base 8 disposed on an inside thereof. A hollow pin 9 is disposed inside the casing 7 and has a flange 11 on an upstream end thereof opposing entering fluid 14. The pin 9 is a hollow thin cylindrical pin made of lightweight material such as metal or plastic.

The pin 9 has an narrow slit or orifice 10 located along one side thereof. Of course, there may be more than one slit 10 and it may be an opening, a slit, a groove, a filter, helically-shaped, etc. depending on the fluid and the desired fluid flow characteristics. Incoming fluid 14 flows into chamber 13 of device 1, contacts pin flange 11, passes through orifice 10, and exits the device 1 through the downstream opening 16 of pin 9 as exit fluid 15.

Pin 9 is biased against incoming fluid 14 with a biasing means 12 which is preferably a circular metal spring. As will be described in more detail below, as the pressure of incoming fluid 14 increases, spring 12 is compressed, pin 9 is pushed downward, and the opening 10 is made smaller by being covered by base 8. Thus, once spring 12 begins to be compressed, increasing pressure will not result in increased flow through device 1.

Figure 4A:
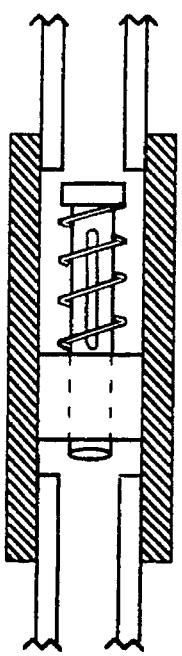
FIGS. 4a–4e depict the operation of the FIG. 3 device.
Figure 4B:
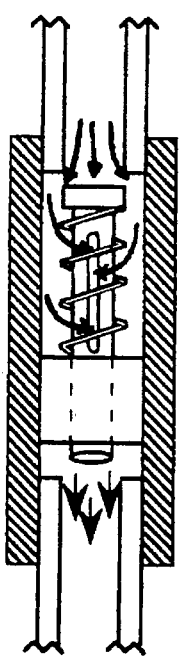
Figure 4C:
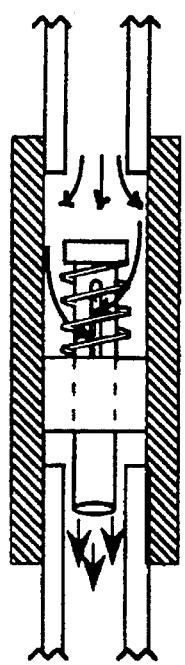
Figure 4D:
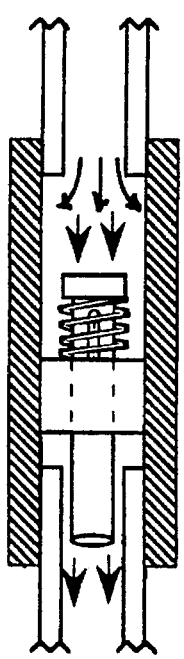
Figure 4E:
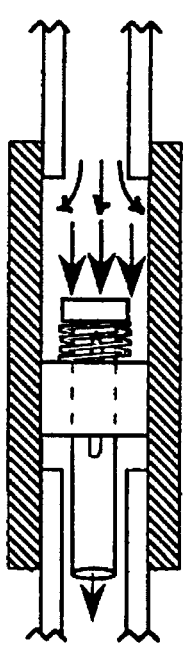

The above-briefly described operation of the FIG. 3 embodiment is depicted more clearly in FIGS. 4a–4e. In FIG. 4a, little or no fluid is flowing and the spring is compressed only by the weight of the pin. In FIG. 4b, fluid begins to flow causing some pressure, but not-enough to compress the spring. In FIG. 4c, increased fluid pressure compresses the spring causing the pin to move downward, covering part of the orifice and restricting flow from the device. In FIG. 4d, increasing pressure compresses the spring to provide an even smaller orifice for fluid to exit device 1. In FIG. 4e, a great deal of fluid pressure compresses the spring to the point where very little fluid will flow through the orifice and out of the device 1.

Figure 5A:
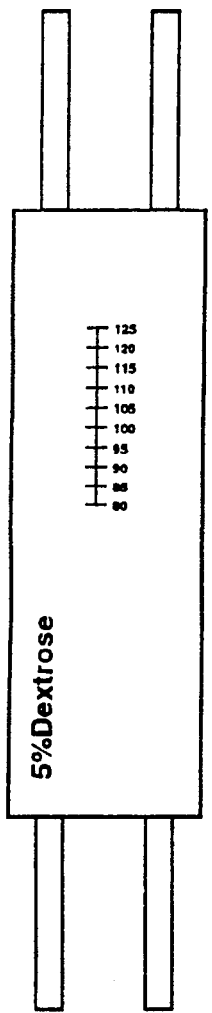
FIGS. 5a–5c depict the outside of the FIG. 3 device for different solutions.
Figure 5B:
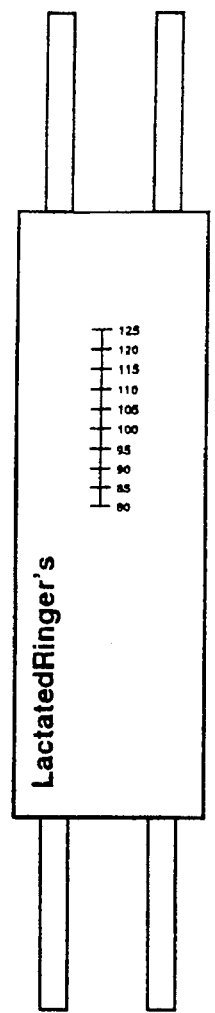
Figure 5C:
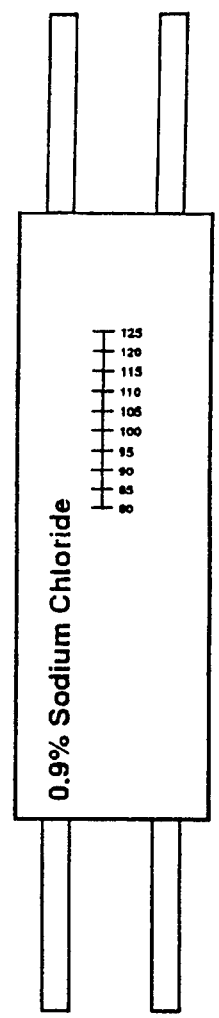

Preferably, the present invention may be provided for a wide variety of viscosities of IV fluids. That is, different springs 12 and/or different orifices 10 may be designed depending upon the viscosity of the IV fluid and its projected flow rate. For example, FIG. 5a depicts a device 1 for 5% Dextrose solution. FIG. 5b depicts the device 1 for Lactated Ringer's solution. FIG. 5c depicts a device 1 for 0.9% Sodium Chloride solution.

The design of a particular device 1 for a given solution must first consider the kind of solution to be infused. Because different infusion solutions have different viscosities, a particular device should only be used in the infusion of the solution for which the device was calibrated. Thus, it is preferred that calibration be carried out for each particular infusion solution.

For practical purposes, the length of the device is limited and should not be more than about 3–6 inches long, and therefore the range of infusion rates cannot be very wide. Thus, one set of devices may be provided for adults and another set for children. As an example, a device with an infusion rate calibration of about 70–150 ml/hr will be designed for adults and a device with an infusion rate calibration of about 40–80 ml/hr will be designed for children. A number of design parameters may be modified in order to calibrate the device for a particular flow rate. While it is possible to vary the inside diameter of the case 7, it is more practical to design a fixed case 7 and to vary bore of the chamber 13, the diameter of pin 9, the strength of the spring 12, and/or the opening of the orifices 10. As a specific example, the linear coefficient of spring 12 will be approximately 7.72 grams/inch for the FIGS. 5a–5c solutions since these solutions have viscosities quite similar to water, and assuming that the diameter of flange 11 is approximately 1/10 inch and that the potential pressure which can be applied to compress the spring 12 is about feet of water.

The size of orifice 10 may also be varied in accordance with the IV fluid viscosity and the desired flow. For example, orifice 10 may be a rectangular slot from about 10–50 mm long by about 1–5 mm wide. Such openings will produce usable flow rates from 60 ml/hr to 260 ml/hr or water-like solutions.

Figure 6:
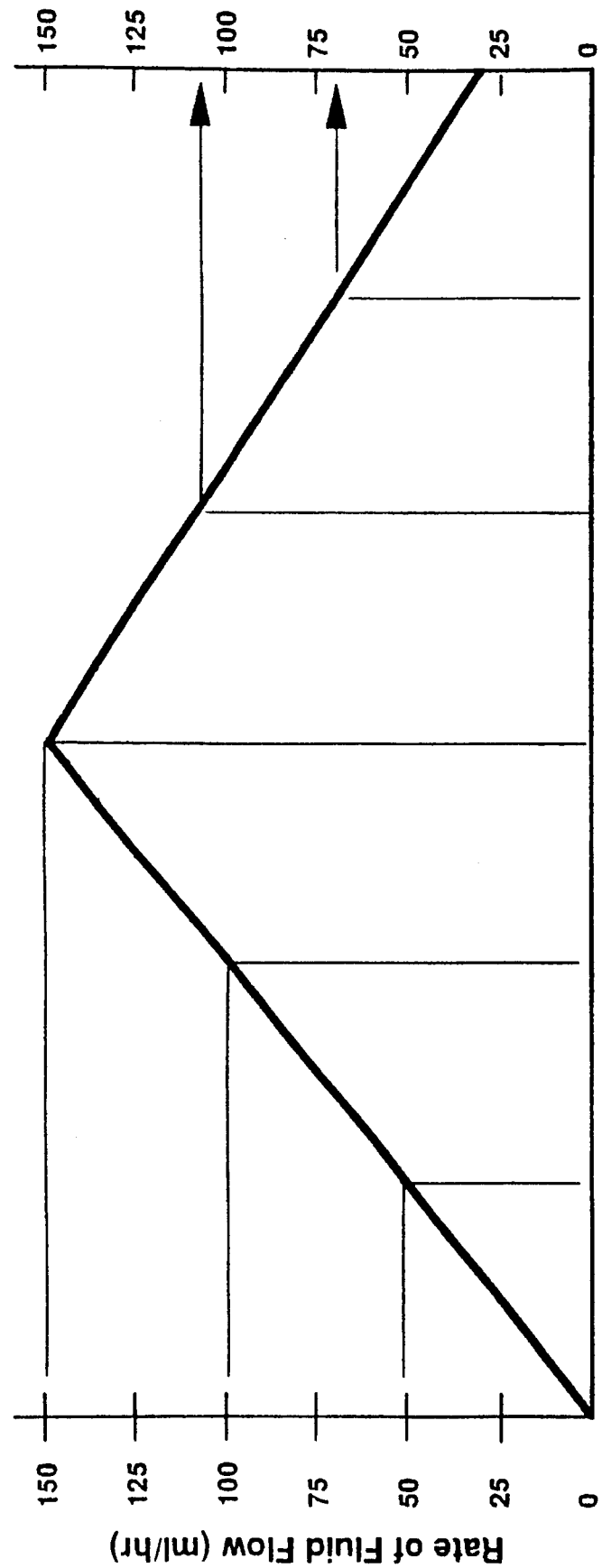
FIG. 6 is a graph depicting the rate of fluid flow for the operating conditions depicted in FIGS. 6A–6G.

FIGS. 6A–6G depict the relationship between the various positions of the manual flow control device 5 and the corresponding positions of the pin 9 inside device 1. In this example, the size of slit 10 is designed to allow a maximum fluid flow rate of 150 ml/hr to exit device 1 without compressing the spring 12 (note that spring 12 is already slightly compressed by the weight of the pin). In FIG. 6A, the manual control device 5 is closed and no fluid enters or leaves device 1 and the flow rate is zero.

In FIG. 6B, the manual control device 5 is about 10% open, allowing a small amount of fluid to enter device 1, but because the fluid entering device 1 is entering at a rate lower than 150 ml/hr, all of the entering fluid is discharged from device 1 without changing the position of pin 9.

In FIG. 6C, the manual control device 5 is about 20% open, allowing more fluid to enter the device than in condition B, but still at a rate below 150 ml/hr. Thus, although more fluid enters and leaves device 1, the position of pin 1 still has not changed.

In FIG. 6D, the manual control device 5 is about 30–40% open, allowing about 150 ml/hr of fluid to enter and exit device 1. Note that at a slightly increased flow rate, the spring 12 will start to compress slightly.

In FIG. 6E, the manual control device 5 is about 60–70% open, and the increased flow rate will cause pressure on the flange so as to compress the spring 12 slightly. The downward movement of pin 9 causes the size of slit 10 to be reduced and the fluid will be discharged from device 1 at a rate less than 150 ml/hr.

In FIG. 6F, the manual control device is 80–90% open, and the pressure inside chamber 13 has increased to cause spring 12 to compress further, reducing the size of slit 10 available for fluid to exit device 1.

In FIG. 6G, the manual control device is fully opened, and the pressure inside chamber 13 has increased to cause spring 12 to compress to reduce the size of slit 10 to its minimum condition. Therefore, the fluid discharge from device 1 has a greatly reduced flow.

Figure 7A:
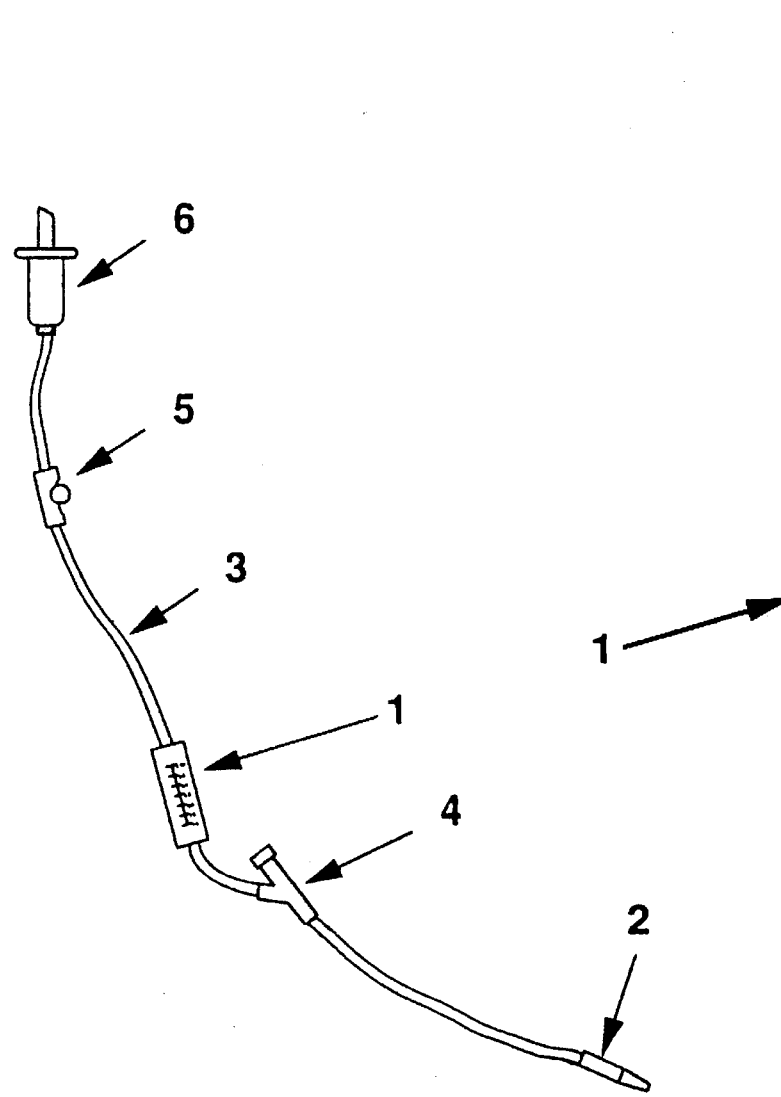
FIGS. 7a and 7b depict a schematic operation of the embodiment of FIG. 3.
Figure 7B:
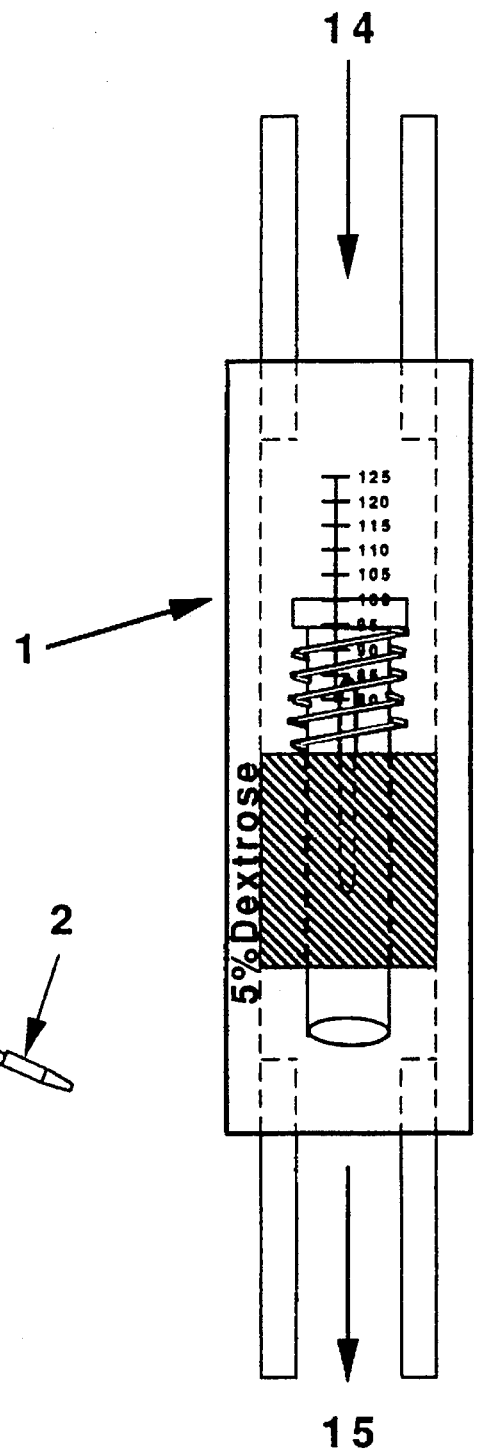

Referring to FIGS. 7a and 7b, the use of the embodiment of FIG. 3 will now be described. For example, suppose the patient is to be infused with 5% Dextrose solution at a rate of 100 ml/hr for 12 hours. First, a device 1 according to FIG. 5a will be chosen and is preferably inscribed or labeled for 5% Dextrose 1. The manual flow control device 5 is closed and the IV container 6 is pierced and suspended 3.5–4 feet above the venipuncture site. The drip chamber 6 is squeezed to establish proper fluid level (half full). Next, the manual flow control device 5 is opened to allow solution to expel air from the line after which the device 5 is again closed.

The male adaptor 2 is then attached to the venipuncture device and the venipuncture is then made. The flow control device 5 is then adjusted so that the level of pin 9 on device 1 coincides with the 100 ml/hr marking on the calibration scale shown in FIG. 7.

A second embodiment according to the present invention will now be described with reference to FIGS. 8–11. Like reference numerals will be used to denote like structure as in the first embodiment. In the second embodiment, the device 1 is designed to be integral with or attachable to the male adaptor 2 shown in FIG. 7.

The casing 7 is again made of clear, transparent plastic so as to be similar to the material used in the construction of male adaptor 2. The casing 7 has four bores or chambers that are interconnected with one another. Bore 23 starts from the top 20 of casing 7 and ends on shoulder 28. Bore 26 starts from shoulder 8 and ends at the top 27 of bore 24. As is clear from FIG. 8*a*, bore 26 contacts an outside surface of pin 9 to prevent liquid from passing therebetween. Bore 24 starts at top 27 and ends at shoulder 31, and bore 15 begins at shoulder 31 and ends at the fluid exit portion 29 of casing 7.

In this embodiment, spring 12 is disposed between the bottom of flange 11 and the shoulder 28, coiling around hollow pin 9. The pin 9 has two slits 10 disposed on opposite sides of the pin. The pin 9 fits snugly into bore 26. In this embodiment, slits 10 have the shape of a tall isosceles triangle where the maximum width is located at the bottom portion, and the smallest width or apex is located at the top portion near flange 11.

Figure 8A:
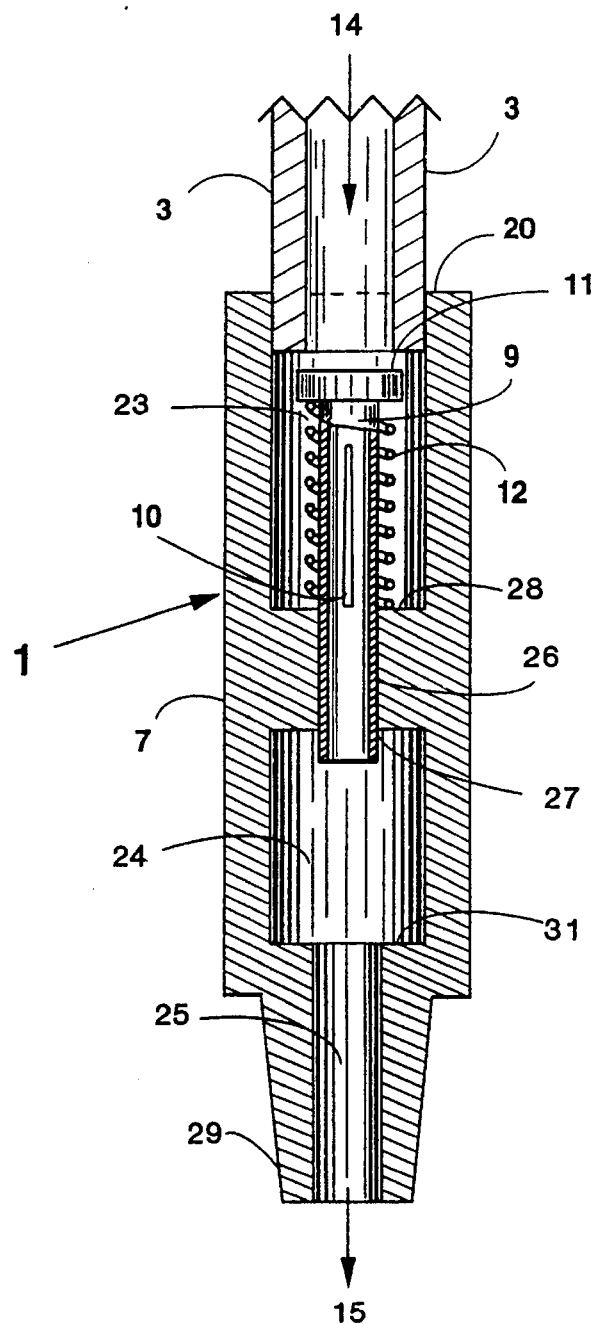
FIGS. 8a and 8b depict a second embodiment according to the present invention.
Figure 8B:
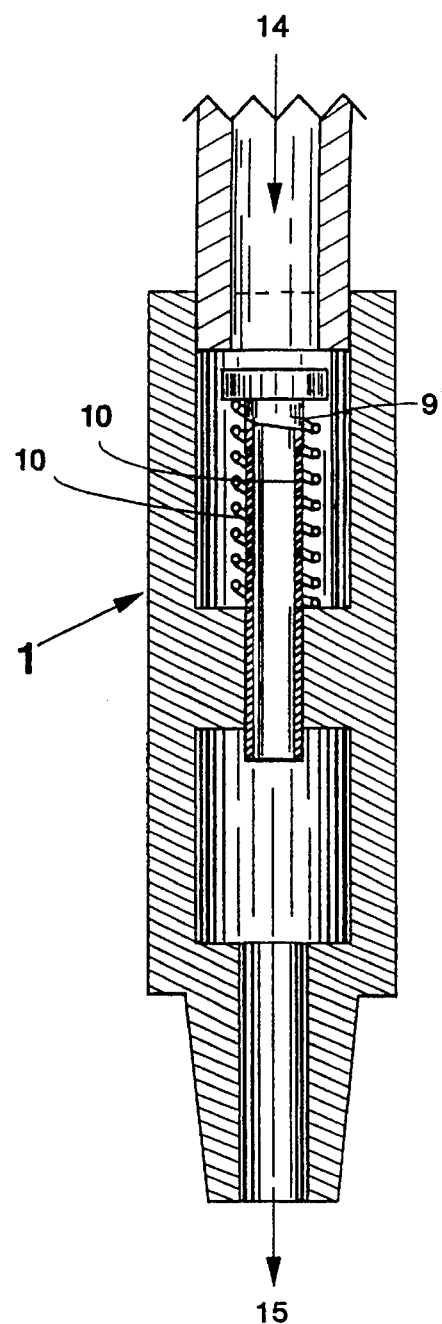

FIG. 8*b* is a cross-section showing that slits 10 are disposed on opposite sides of pin 9.

The bottom portion 29 of casing 7 is specifically designed so that the device 1 may replace the male adaptor 2 shown in FIG. 2. Thus, the tip 29 of this embodiment of the present invention will now become the male adaptor of the IV set shown in FIG. 2.

Figure 9A:
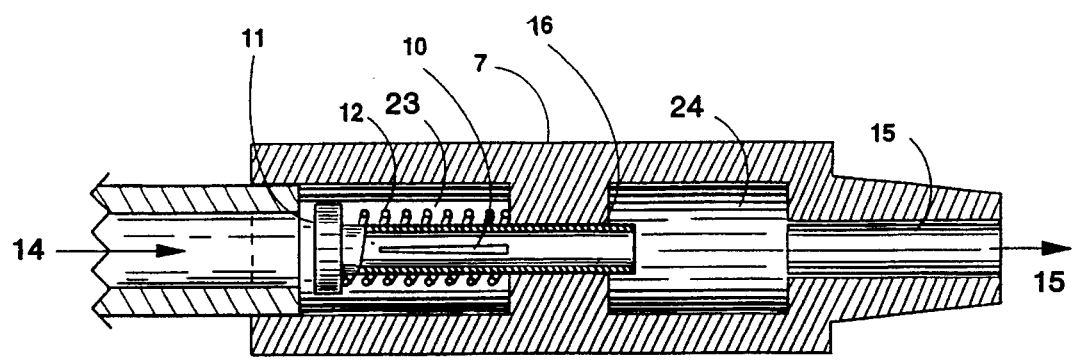
FIGS. 9a–9c depict the operation of the FIG. 8a embodiment.
Figure 9B:
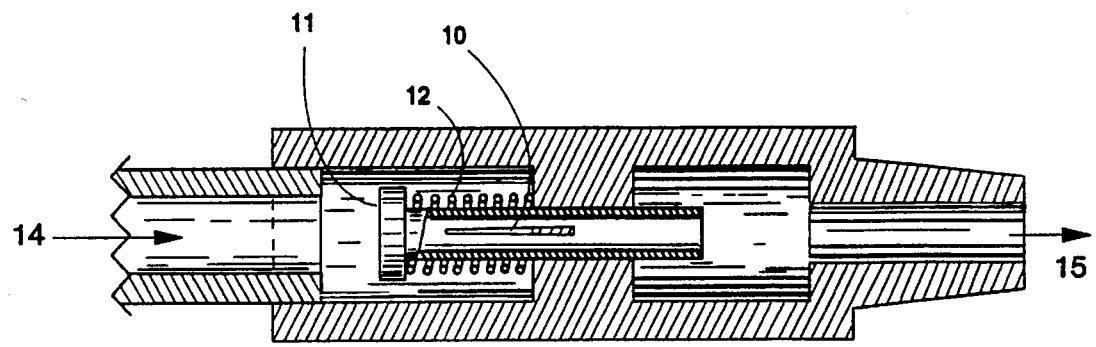
Figure 9C:
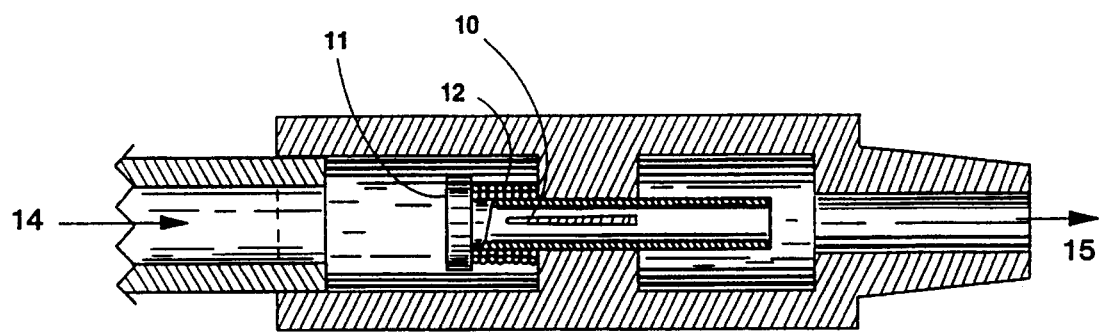

Referring to FIGS. 9*a*–9*c*, the operation of this embodiment can readily be understood. As with the first embodiment, the rate of flow is regulated by the use of the manual flow control device 5. Starting from the closed position of the manual control device 5 and progressively opening same, FIG. 9*a* shows the whole area of the slits 10 are within the bore 23. This condition occurs when the rate of fluid 14 entering device 1 is from 0 to the maximum laminar flow rate which will not cause pressure to build inside bore 23 which would cause spring 12 to compress. After retaining this maximum laminar flow rate, if manual control device is opened a little more, fluid pressure will start to build inside bore 23 and will compress spring 12, moving pin 9 into bore 24. Thus, the area of slits 10 within bore 23 will be reduced, as shown in FIG. 9*b*. Accordingly, the amount of fluid flowing from bore 23 through bore 26 to bore 24 will be reduced as compared with the flow in FIG. 9*a*.

If the manual control device 5 is opened more, the condition of FIG. 9*c* will obtain wherein increased fluid pressure inside bore 23 will further compress spring 12, further reducing the area of slits 10 exposed to bore 23. Now, even less fluid will flow from bore 23 through bore 26 to bore 24.

Figure 10A:
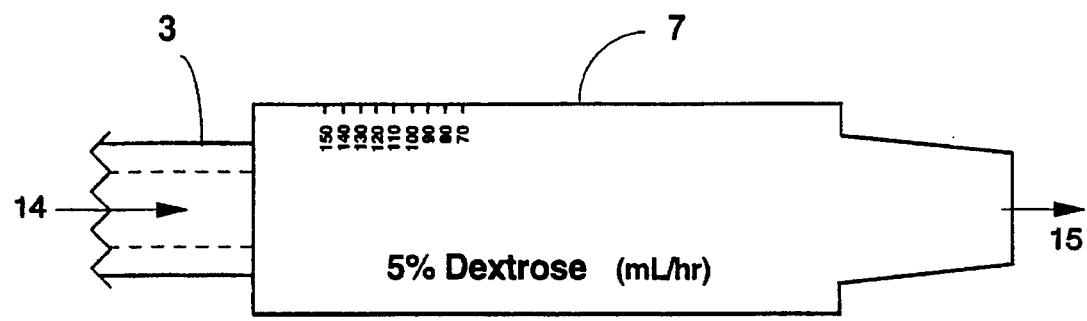
FIGS. 10a and 10b depict the outside of the FIG. 8a embodiment for different solutions.
Figure 10B:
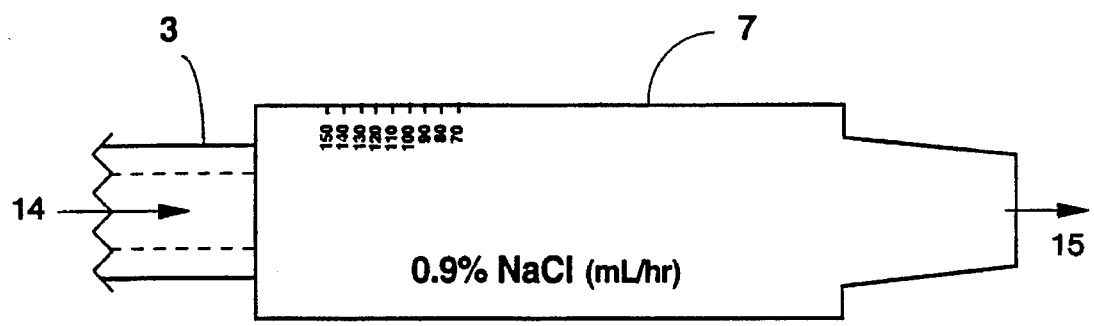

FIGS. 10*a*–10*b* depict calibrated infusion rates for given solutions. Preferably, each device 1 will be calibrated for a specific solution to be infused.

Figures 11A, 11B:
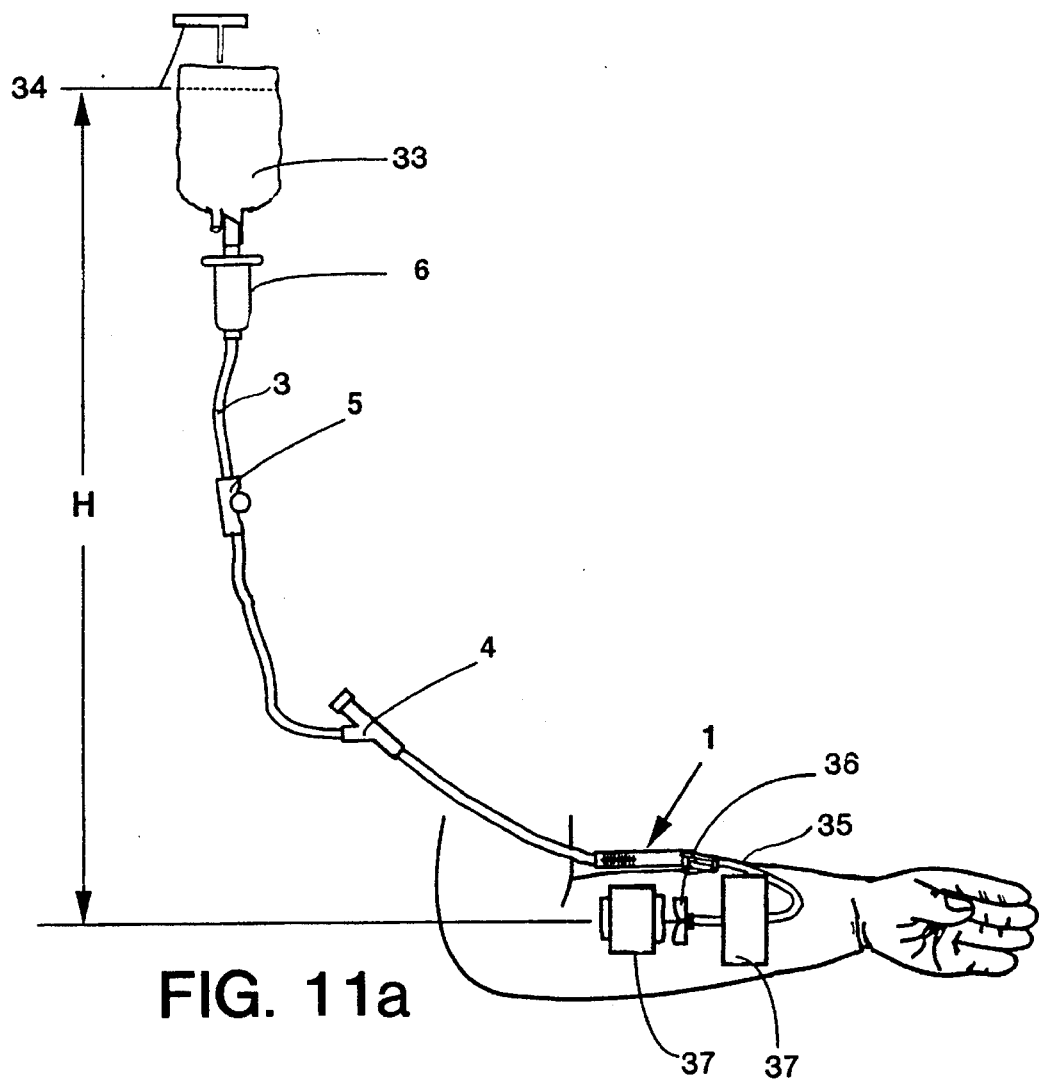
FIGS. 11a and 11b depict the in-use operation of the FIG. 8 embodiment.

FIG. 11*a* depicts a typical set-up for the automatic IV flow control device according to the present invention. The IV fluid bag 33 is supported from a support 24 at a height H of about 3–4 ft. above the venipuncture site. The fluid passes through drip chamber 6, line 3, manual control device 5, Y-insertion device 4, and then to device 1. Device 1 is coupled to a venipuncture device 35, which transmits the fluid exiting device 1 to IV needle 36 which is inserted in the patient's arm. As is well known, adhesive patches 37 secure the IV needle 36 to the patient.

FIG. 11*b* depicts a close-up of device 1 from FIG. 11*a*. In this example, a 5% Dextrose solution is being infused at approximately 120 ml/hr as is shown by the top of the pin flange in registration with the 120 ml/hr mark.

Thus, what has been described is an inexpensive, easy-to-operate automatic IV flow control device which will safely and accurately deliver controlled amounts of IV fluid to a patient.

The individual components shown in outline or designated by blocks in the attached drawings are all well-known in the IV control arts and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An intravenous fluid flow control device comprising:

a rigid casing having a fluid entrance and a fluid exit, a portion of said casing comprising a flow restrictor;

a pin disposed inside said casing and axially movable within said flow restrictor, said pin having an interior passageway and at least one upstream opening for a fluid to pass from said casing fluid entrance to said interior passageway of said pin, said upstream opening being elongated in a direction parallel to a pin longitudinal axis, the pin elongated opening being axially movable within said flow restrictor to variably restrict a flow of the fluid passing through the interior passageway of said pin, said pin having a downstream opening for fluid to pass from the interior passageway of said pin to exit said device; and biasing means for biasing said pin against a pressure of the fluid entering from said casing fluid entrance to cause said pin elongated opening to move with respect to said fluid restrictor to variably control the flow of fluid through said pin interior passageway such that, as the fluid pressure variably increases to a predetermined value, the fluid flow through the elongated opening also increases, and, as the fluid pressure variably increases the above-predetermined value, the elongated opening moves within the flow restrictor causing the flow fluid through the elongated opening to decrease.

2. A device according to claim 1, wherein the biasing means allows the pin elongated opening to move further with respect to said fluid restrictor to further reduce the flow of fluid through said pin interior passageway as the fluid pressure on the pin increases.

3. A device according to claim 1, further comprising a male adaptor coupled to said casing and in liquid communication with said fluid exit, said male adaptor being dimensioned to couple to a venipuncture device.

4. A device according to claim 1, wherein said casing comprises a transparent plastic having calibrated markings thereon.

5. A device according to claim 1, wherein said pin comprises a hollow pin, and wherein said interior passageway comprises at least one axially-disposed elongated slit in said hollow pin.

6. A device according to claim 1, wherein said biasing means comprises a helical metal spring.

7. An intravenous fluid flow control apparatus comprising:

a rigid casing having a fluid entrance and a fluid exit;

a fluid restrictor disposed inside said casing;

a pin disposed inside said casing and axially movable with respect to said fluid restrictor, said pin having an interior passageway and at least one upstream opening for a fluid to pass from said casing fluid entrance to said interior passageway of said pin, said upstream opening being elongated in a direction parallel to a pin longitudinal axis, the pin elongated opening being axially movable within said fluid restrictor to variably restrict a flow of the fluid passing through the interior passageway of said pin, said pin having a downstream opening for the fluid to pass from the interior passageway of said pin to said casing fluid exit;

a pin flange disposed on an upstream end of said pin for contacting the fluid entering from said casing fluid entrance; and biasing means for biasing said pin flange against the fluid entering from said casing fluid entrance to cause said pin elongated opening to move with respect to said fluid restrictor such that, as the fluid pressure variably increases to a predetermined value, the fluid flow through the elongated opening also increases, and, as the fluid pressure variably further increases above the predetermined value, the elongated opening moves within the fluid restrictor causing the fluid flow through the elongated opening to decrease.

8. Apparatus according to claim 7, wherein said biasing means comprises a spring, and the predetermined value of fluid pressure on the pin flange equals an amount of pressure on said spring required to begin compressing the spring.

9. Apparatus according to claim 7, wherein said casing comprises a transparent plastic having fluid flow calibration markings thereon.

10. Apparatus according to claim 7, wherein said casing has two interior chambers connected by a narrow bore, the narrow bore comprising said fluid restrictor, said pin sliding axially within said narrow bore as the fluid pressure increases over the predetermined value.

11. Apparatus according to claim 7, wherein said pin comprises a hollow cylinder, said upstream opening comprising two axially-disposed elongated slits on opposite sides of said cylinder, said downstream opening comprising a circular opening at an end of said cylinder.

12. Apparatus according to claim 7, wherein said pin upstream opening and said biasing means are calibrated for a particular viscosity of fluid to be passed through said fluid flow control apparatus.

13. Apparatus according to claim 7, wherein a downstream portion of said casing is dimensioned to be coupleable to a venipuncture device.

14. Intravenous fluid flow control apparatus comprising:

a rigid plastic casing having a fluid entrance and a fluid exit;

a fluid restrictor disposed inside of said casing;

a hollow cylindrical pin disposed inside said casing and axially movable With respect to said fluid restrictor, said pin having an interior and a flange which is disposed on an upstream end thereof for contacting a fluid entering from said casing fluid entrance, said pin having at least one slot elongated in a direction parallel to a longitudinal axis of the pin and disposed downstream of said pin flange to allow fluid to pass from said casing fluid entrance to the interior of said pin, said pin elongated slot being disposed with respect to said fluid restrictor to variably restrict a flow of fluid passing to the interior of said pin, said pin being open at a downstream end thereof for the fluid to pass from the interior of the pin to said casing fluid exit; and a spring disposed between said pin flange and said casing fluid exit to bias the pin flange against a pressure of the fluid entering from the casing fluid entrance to cause the pin elongated slot to move with respect to the fluid restrictor such that, as the fluid pressure variably increases to a predetermined value, the fluid flow through the elongated opening also increases and, as the fluid pressure variably increases above the predetermined value, the elongated opening moves within the fluid restrictor causing the fluid flow through the elongated opening to decrease.

15. Apparatus according to claim 14, wherein said rigid casing has fluid flow calibration marks disposed thereon, said pin flange registering with the calibration marks to indicate the fluid flow through the apparatus.

16. Apparatus according to claim 14, further comprising a venipuncture male coupling disposed on a downstream portion of said rigid casing to couple said apparatus to a venipuncture device.

17. Apparatus according to claim 14, wherein said rigid casing and said fluid restrictor are integrally formed.

18. Apparatus according to claim 14, wherein said biasing means comprises a helical metal spring.

19. Apparatus according to claim 14, wherein said spring and said pin slots are calibrated to provide fluid flow rates in a predetermined range within a band of about 70 ml/hr through about 150 ml/hr.

20. Apparatus according to claim 14, wherein said spring and said pin slot are calibrated for at least one of a 5% Dextrose solution, Lactated Ringers solution, and a 0.9% sodium chloride solution.

21. Apparatus according to claim 1, wherein when the pin is displaced downstream into the flow restrictor by a maximum amount, the minimum fluid flow continues through the device.

* * * * *

UNITED STATES PATENT AND TRADEMARK OFFICE
CERTIFICATE OF CORRECTION

PATENT NO. : 5,514,110  
DATED : May 7, 1996  
INVENTOR(S) : EUTIQUIO L. TEH

Page 1 of 2

It is certified that error appears in the above-indentified patent and that said Letters Patent is hereby corrected as shown below:

Column 1,  
    line 3, "continuation in part" should read --continuation-in-part--;  
    line 11, "prior" should read --Prior--; and  
    line 63, "valve" (second occurrence) should read --the valve--.  
Column 2,  
    line 49, "FIGS. 6A-6G" should read --FIGS. 6a-6g--; and  
    line 50, FIGS. 6A-6G" should read --FIGS. 6a-6g--.  
Column 3,  
    line 3, "(now" should read --(not--;  
    line 16, "an" should read --a--;  
    line 36, "not-enough" should read --not enough--; and  
    line 50, "the" should read --a--.  
Column 4,  
    line 12, "feet" should read --3 feet--;  
    line 19, "FIGS. 6A-6G" should read --FIGS. 6a-6g--;  
    line 25, "FIG. 6A," should read --FIG. 6a,--;  
    line 28, "FIG. 6B,"s should read --FIG. 6b,--;  
    line 34, "FIG. 6C," should read --FIG. 6c,--;  
    line 38, "pin 1" should read --pin 9--;  
    line 39, "FIG. 6D," should read --FIG. 6d,--;  
    line 43, "FIG. 6E," should read --FIG. 6e,--;  
    line 49, "FIG. 6F," should read --FIG. 6f,--;

line 53, "FIG. 6G," should read --FIG. 6g,--.

UNITED STATES PATENT AND TRADEMARK OFFICE
CERTIFICATE OF CORRECTION

PATENT NO. : 5,514,110
DATED : May 7, 1996
INVENTOR(S) : EUTIQUIO L. TEH

It is certified that error appears in the above-indentified patent and that said Letters Patent is hereby corrected as shown below:

<u>Column 5</u>,
    line 18, "shoulder 8" should read --shoulder 28--.
<u>Column 8</u>,
    line 10, "With" should read --with--; and
    line 55, "Apparatus" should read --A device--.

Signed and Sealed this

Eighteenth Day of March, 1997

*Attest:*

BRUCE LEHMAN

*Attesting Officer*     *Commissioner of Patents and Trademarks*